United States Patent
Boelens et al.

(10) Patent No.: US 7,288,688 B2
(45) Date of Patent: Oct. 30, 2007

(54) PROCESS FOR PREPARING STYRENE

(75) Inventors: Minne Boelens, Amsterdam (NL); Andrew David Horton, Amsterdam (NL); Timothy Michael Nisbet, Amsterdam (NL); Aart Bartus Van Oort, Amsterdam (NL)

(73) Assignee: Shell Oil Company, Houston, TX (US)

( * ) Notice: Subject to any disclaimer, the term of this patent is extended or adjusted under 35 U.S.C. 154(b) by 526 days.

(21) Appl. No.: 11/001,463

(22) Filed: Dec. 1, 2004

(65) Prior Publication Data

US 2005/0143611 A1 Jun. 30, 2005

(30) Foreign Application Priority Data

Dec. 2, 2003 (EP) ................... 03257573

(51) Int. Cl.
*C07C 1/207* (2006.01)
(52) U.S. Cl. ...................... 585/437; 585/436
(58) Field of Classification Search ............ 585/437, 585/436
See application file for complete search history.

(56) References Cited

U.S. PATENT DOCUMENTS

| 3,526,674 A | 9/1970 | Becker et al. ............. 260/669 |
| 5,639,928 A | 6/1997 | Dubner et al. ............. 585/435 |
| 2004/0010172 A1* | 1/2004 | Horton et al. ............. 585/436 |

FOREIGN PATENT DOCUMENTS

| EP | 1077916 | 2/2001 |
| GB | 1343177 | 9/1971 |

OTHER PUBLICATIONS

Written Opinion of the International Searching Authority dated May 23, 2005.
International Search Report dated Apr. 27, 2005.
TS1030 - Patent application No. EP 03251123.0 filed Feb. 25, 2003.

* cited by examiner

*Primary Examiner*—Thuan Dinh Dang

(57) ABSTRACT

A process for preparing styrene by contacting a gaseous feed which contains 1-phenylethanol and at least 0.1% wt of phenol and/or ethylphenol with a heterogeneous dehydration catalyst in the presence of at least 0.40% wt of benzylalcohol and at a molar ratio of benzylalcohol to total amount of phenol and ethylphenol of at least 0.8.

12 Claims, No Drawings

PROCESS FOR PREPARING STYRENE

FIELD OF THE INVENTION

The invention pertains to a process for preparing styrene by contacting gaseous 1-phenylethanol with a heterogeneous dehydration catalyst.

BACKGROUND OF THE INVENTION

A commonly known method for manufacturing styrene is the coproduction of propylene oxide and styrene starting from ethylbenzene. In general, such process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl-ethanol, and (iii) converting the 1-phenyl-ethanol into styrene by dehydration using a suitable dehydration catalyst. The present invention particularly focuses on the last step, i.e. the dehydration of 1-phenyl-ethanol to yield styrene.

The synthesis of styrene is important because this product functions as starting material for valuable commercial products such as plastics and the like. A disadvantage of these processes is the formation of heavy by-products especially if these by-products are formed from valuable starting compounds. Phenol and ethylphenol are generally present in the feed to the dehydration unit. Both phenol and ethylphenol have been observed to react with 1-phenylethanol thereby forming mono- and polyalkylated phenols. This not only results in heavy by-product being formed but also results in the consumption of a valuable starting compound. A solution to this problem would be the removal of phenol and ethylphenol from the feed before dehydration. However, phenol and ethylphenol are difficult to separate from 1-phenylethanol and such separation process would be cumbersome and expensive.

SUMMARY OF THE INVENTION

The process of the present invention is directed to a process for preparing styrene by contacting a gaseous feed which contains 1-phenylethanol and at least 0.1% wt of phenol and/or ethylphenol with a heterogeneous dehydration catalyst in the presence of at least 0.40% wt of benzylalcohol and at a molar ratio of benzylalcohol to total amount of phenol and ethylphenol of at least 0.8.

DETAILED DESCRIPTION OF THE INVENTION

It has been found that benzylalcohol may reduce the amount of valuable 1-phenylethanol reacted with phenol and/or ethylphenol during gas phase dehydration. It was found that the phenol and/or ethylphenol reacted with benzylalcohol if benzylalcohol was present during the dehydration. Thus, the presence of benzylalcohol lowers the amount of 1-phenylethanol which reacts with phenol and/or ethylphenol.

The dehydration of 1-phenylethanol into styrene according to the present invention is carried out in the gas phase. In principle, any combination of conditions may be applied as long as the 1-phenylethanol is substantially in the gas phase. The dehydration conditions which are generally applied include reaction temperatures of from 150° C. to 350° C., more specifically from 210° C. to 330° C., preferably from 280° C. to 320° C. The pressure generally is in the range of from 0.1 to $10 \times 10^5$ N/m².

The dehydration process will generally be carried out in a reactor containing one or more beds of heterogeneous catalyst. The feed will usually be led over the catalyst in once-through mode.

In principle, any heterogeneous catalyst may be used in the present process. Catalysts which are well known to be suitable comprise alumina, alkali alumina, aluminium silicates and H-type synthetic zeolites. Preferably, an alumina catalyst is used in the present process. A catalyst which is especially preferred is a dehydration catalyst comprising shaped alumina catalyst particles having a surface area (BET) in the range of from 80 to 140 m²/g and a pore volume (Hg) in the range of from 0.35 m²/g to 0.65 ml/g, of which 0.03 ml/g to 0.15 ml/g is in pores having a diameter of at least 1000 nm. This catalyst has been described extensively in EP-A-1077916. A further catalyst which is especially suitable for use in the present invention is a dehydration catalyst comprising shaped alumina catalyst particles having a surface area (BET) of from 80 m²/g to 140 m²/g and a pore volume (Hg) of more than 0.65 ml/g described in detail in European patent application 03251123.0.

The 1-phenylethanol feed for use in the present invention may be prepared by different process. A process for preparing suitable 1-phenylethanol feed comprises contacting propene and ethylbenzene hydroperoxide to obtain propylene oxide and 1-phenylethanol. Therefore, the present invention is also directed to (i) contacting propene and ethylbenzene hydroperoxide to obtain propylene oxide and 1-phenylethanol, (ii) separating 1-phenylethanol from the reaction mixture obtained in step (i), and (iii) dehydrating 1-phenylethanol obtained in step (ii) according to the present invention. The ethylbenzene hydroperoxide will usually be prepared by reacting ethylbenzene with oxygen or air.

Contaminants which are present in the 1-phenylethanol feed may be formed during the preparation of the ethylbenzene hydroperoxide and when contacting propene with ethylbenzene hydroperoxide. The amount of contaminants which end up in the feed to the dehydration unit depends on the subsequent separation and purification steps. A further source of contaminants are recycle streams. Part of the reaction mixture obtained in the dehydration unit is usually sent back to the dehydration unit after further conversion and substantial purification. An example is a fraction containing a relatively large amount of methylphenylketone. Methylphenylketone may be formed as a by-product in the manufacture of 1-phenylethanol. The fraction containing methylphenylketone may be hydrogenated to convert methylphenylketone into 1-phenylethanol and subsequently may be recycled to the dehydration unit.

The feed for the present process contains at least 0.1% wt of phenol and ethylphenol. Phenol and ethylphenol behave in a similar fashion in the process according to the present invention. Both tend to be present in 1-phenylethanol containing feeds which are generally available. The amount is based on the total amount of phenol and of ethylphenols present based on total amount of feed. The presence of phenol and ethylphenols is especially disadvantageous if they are present in relatively large quantities such as from 0.2% wt to 2% wt, more specifically from 0.3% wt to 1% wt.

It was found that the presence of benzylalcohol ensures that phenol and/or ethylphenol consume less 1-phenylethanol. In order to be beneficial, the amount of benzylalcohol present should be at least 0.40% wt and additionally the molar ratio of benzylalcohol to total amount of phenol and ethylphenol should be at least 0.8. The specific amount of benzylalcohol which preferably is present in the process according to the present invention depends on the total amount of phenol and ethylphenol which is present in the feed. Preferably, the molar ratio of benzylalcohol to phenol and ethylphenol during the contact is at least 0.9, more specifically at least 1.0. It is disadvantageous if too little benzylalcohol is present as this results in an increase of the reaction of phenol and/or ethylphenol with 1-phenylethanol. However, too much benzylalcohol is also disadvantageous as it does not give a further improvement. Generally, it is preferred that at most 3% wt of benzylalcohol is present, more specifically at most 2% wt, more specifically at most 1.5% wt, most specifically at most 1% wt. The molar ratio of benzylalcohol to phenol and ethylphenol during the contact generally is at most 10, more specifically at most 5. A preferred molar ratio of benzylalcohol to phenol during the contact has been found to be from 1 to 5, most preferably from 1.5 to 4.

Limited amounts of benzylalcohol tend to be present in conventional 1-phenylethanol streams. The exact amount of benzylalcohol depends on the process set-up which is applied. Typically, a 1-phenylethanol feed, for a dehydration unit contains less than 0.40% wt of benzylalcohol. Therefore, a conventional 1-phenylethanol stream as such will contain too little benzylalcohol for use in the present invention. The feed for use in the present invention contains at least 0.40% wt of benzylalcohol, more specifically at least 0.45% wt of benzylalcohol, preferably at least 0.50% wt of benzylalcohol. The amount of benzylalcohol may be increased in any way known to be suitable to someone skilled in the art. It is possible to add benzylalcohol as such. However, this is generally a relatively expensive and cumbersome method.

An advantageous process for increasing the benzylalcohol content of the dehydration unit comprises hydrogenation of the contaminant benzaldehyde into benzylalcohol and recycling the benzylalcohol thus obtained to the dehydration unit. A specific process would comprise (a) contacting a gaseous feed which contains 1-phenylethanol and at least 0.1% wt of phenol and/or ethylphenol with a heterogeneous dehydration catalyst in the presence of at least 0.40% wt of benzylalcohol and at a molar ratio of benzylalcohol to total amount of phenol and ethylphenol of more than 0.8 to obtain a reaction mixture containing styrene, benzaldehyde and methylphenylketone, (b) separating styrene from the reaction mixture obtained in step (a), (c) contacting at least part of the reaction mixture containing benzaldehyde and methylphenylketone obtained in step (b) with hydrogen in the presence of a hydrogenation catalyst to obtain a reaction mixture containing benzylalcohol and 1-phenylethanol, and (d) recycling at least part of the mixture obtained in step (c) to step (a).

The benzaldehyde and methylphenylketone present in the product of step (a) may be by-products of the dehydration reaction of step (a), may be introduced into step (a) by one or more recycle streams and/or may be present in the 1-phenylethanol feed of step (a).

The amount of benzylalcohol, phenol and ethylphenol present in the 1-phenylethanol feed is taken on the total amount of streams which are fed to the dehydration unit including recycle streams which may be added to the dehydration reactor separate from the main 1-phenylethanol feed.

The reaction mixture obtained by the process of the present invention may be processed further in any way known to someone skilled in the art. Even if there is no recycle of benzaldehyde converted into benzylalcohol, it is generally advantageous if styrene is separated from the reaction mixture obtained in the dehydration unit, and at least part of the reaction mixture containing a substantial amount of methylphenylketone is hydrogenated to 1-phenylethanol. The 1-phenylethanol thus obtained may be recycled to the dehydration unit. Further separation and purification steps depend on the products required and on the exact circumstances.

The invention is further illustrated by the following non-limiting examples.

COMPARATIVE EXAMPLE 1

A star-shaped catalyst having the physical properties as indicated in Table I was used in a microflow unit consisting of a 13 mm diameter plugflow reactor, 1-phenyl-ethanol feed facilities and product vapor condensing facilities.

TABLE I

| Catalyst properties | |
|---|---|
| Shape | star |
| Surface area ($m^2/g$) | 99 |
| Pore Volume (ml/g) | 0.57 |
| Pore Volume >1000 nm (ml/g) | 0.07 |
| Side Crushing Strength (N) | 61 |
| Bulk Crushing Strength (MPa) | 1.1 |
| Bulk density (ml/g) | 0.71 |
| Particle diameter (mm) | 3.6 |

The feedstock consisted of 1.0% wt of phenol in 1-phenyl-ethanol. The outlet stream of the micro flow unit was liquefied by condensation and the resulting two phase liquid system was analyzed by means of gas chromatographic analysis.

The dehydration experiment was carried out at standard test conditions of 1.0 bara pressure and a temperature of 300° C. The feed rate of 1-phenyl-ethanol was maintained at 30 grams per hour and the reactor tube was loaded with 20 $cm^3$ catalyst, which corresponds to 13.8 grams of star-shaped catalyst particles having a length/diameter ratio of about 1.1.

Styrene was removed from the reaction mixture obtained and the compounds in the remainder of the reaction mixture were determined. The amounts of the following compounds were measured:

molar amount of phenyl-CH—$CH_3$ moieties per mole of phenol converted molar amount of phenyl-$CH_2$ moieties per mole of phenol converted molar percentage of phenol converted molar percentage of benzylalcohol converted The phenyl-CH—$CH_3$ moiety is formed when 1-phenylethanol has reacted with phenol or ethylphenol.

The phenyl-$CH_2$ moiety is formed when benzylalcohol has reacted with phenol or ethylphenol.

The presence of the phenyl-CH—$CH_3$ moiety and the phenyl-$CH_2$ moiety was determined by $^1H$ NMR. The value of more than 1 is attributed to di- and tri-alkylated phenols and di-alkylated ethylphenols.

The results are indicated in Table II.

EXAMPLE 1

Comparative Example 1 was repeated except that the feedstock consisted of 1.0% wt of phenol and 2.0% wt of benzylalcohol in 1-phenyl-ethanol.

The results are indicated in Table II.

EXAMPLE 2

Comparative Example 1 was repeated except that the feedstock consisted of 0.3% wt of phenol and 0.6% wt of benzylalcohol in 1-phenyl-ethanol.

The results are indicated in Table II.

COMPARATIVE EXAMPLE 2

Comparative Example 1 was repeated except that the feedstock consisted of 1.0% wt of 4-ethylphenol in 1-phenyl-ethanol.

The results are indicated in Table II.

EXAMPLE 3

Comparative Example 2 was repeated except that the feedstock consisted of 1.0% wt of 4-ethylphenol and 2.0% wt of benzylalcohol in 1-phenyl-ethanol.

The results are indicated in Table II.

EXAMPLE 4

Comparative Example 2 was repeated except that the feedstock consisted of 0.3% wt of 4-ethylphenol and 0.6% wt of benzylalcohol in 1-phenyl-ethanol.

The results are indicated in Table II.

TABLE II

| Ex. | Feed (% wt in 1-phenyl-ethanol) | phenyl-CH—CH$_3$ moiety | phenyl—CH$_2$ moiety | 4-(ethyl) phenol converted (%) | benzylalcohol converted (%) |
|---|---|---|---|---|---|
| Comp. 1 | 1.0 phenol | 1.88 | | 92 | |
| 1 | 1.0 phenol 2.0 benzylalcohol | 1.71 | 0.49 | 96 | 63 |
| 2 | 0.3 phenol 0.6 benzylalcohol | 1.73 | 0.54 | 97 | 64 |
| Comp. 2 | 1.0 ethylphenol | 1.64 | | 91 | |
| 3 | 1.0 ethylphenol 2.0 benzylalcohol | 1.33 | 0.60 | 100 | 60 |
| 4 | 0.3 ethylphenol 0.6 benzylalcohol | 1.34 | 0.54 | 100 | 60 |

We claim:

1. A process for preparing styrene by contacting a gaseous feed which contains 1-phenylethanol and at least 0.1% wt of phenol and/or ethylphenol with a heterogeneous dehydration catalyst in the presence of at least 0.40% wt of benzylalcohol and at a molar ratio of benzylalcohol to total amount of phenol and ethylphenol of at least 0.8.

2. The process of claim 1 wherein the heterogeneous dehydration catalyst is an alumina catalyst.

3. The process of claim 1 wherein the process is performed at 150° C. to 350° C. and at a pressure in the range of from 0.1 to $10 \times 10^5$ N/m$^2$.

4. The process of claim 1 wherein the molar ratio of benzylalcohol to total amount of phenol and ethylphenol is from 1 to 5.

5. A process for preparing styrene, which process comprises:
   (i) contacting propene with ethylbenzene hydroperoxide in the presence of a heterogeneous catalyst to obtain propylene oxide and 1-phenylethanol;
   (ii) separating 1-phenylethanol from the reaction mixture obtained in step (i); and,
   (iii) contacting a feed mixture comprising the 1-phenylethanol and at least 0.1% wt of phenol and/or ethylphenol with a heterogeneous dehydration catalyst in the presence of at least 0.40% wt of benzylalcohol and at a molar ratio of benzylalcohol to total amount of phenol and ethylphenol of at least 0.8.

6. The process of claim 5 wherein the heterogeneous dehydration catalyst is an alumina catalyst.

7. The process of claim 5 wherein step (iii) is performed at 150° C. to 350° C. and at a pressure in the range of from 0.1 to $10 \times 10^5$ N/m$^2$.

8. The process of claim 5 wherein in step (iii) the molar ratio of benzylalcohol to total amount of phenol and ethylphenol is from 1 to 5.

9. A process for preparing styrene which process comprises:
   a) contacting a gaseous feed which contains 1-phenylethanol and at least 0.1% wt of phenol and/or ethylphenol with a heterogeneous dehydration catalyst in the presence of at least 0.40% wt of benzylalcohol and at a molar ratio of benzylalcohol to total amount of phenol and ethylphenol of more than 0.8 to obtain a reaction mixture containing styrene, benzaldehyde and methylphenylketone;
   b) separating styrene from the reaction mixture obtained in step (a);
   c) contacting at least part of the reaction mixture containing benzaldehyde and methylphenylketone obtained in step (b) with hydrogen in the presence of a hydrogenation catalyst to obtain a reaction mixture containing benzylalcohol and 1-phenylethanol; and,
   d) recycling at least part of the mixture obtained in step (c) to step (a).

10. The process of claim 8 in which process the molar ratio of benzylalcohol to total amount of phenol and ethylphenol is of from 1 to 5.

11. The process of claim 8 wherein the heterogeneous dehydration catalyst is an alumina catalyst.

12. The process of claim 8 wherein step (a) is performed at 150° C. to 350° C. and at a pressure in the range of from 0.1 to $10 \times 10^5$ N/m$^2$.

* * * * *